United States Patent [19]

Edwards et al.

[11] Patent Number: 5,769,846

[45] Date of Patent: *Jun. 23, 1998

[54] ABLATION APPARATUS FOR CARDIAC CHAMBERS

[75] Inventors: Stuart D. Edwards, 1681 Austin Ave., Los Altos, Calif. 94024; Hugh R. Sharkey, Redwood Shores, Calif.

[73] Assignee: Stuart D. Edwards, Los Altos, Calif.

[*] Notice: The term of this patent shall not extend beyond the expiration date of Pat. No. 5,681,308.

[21] Appl. No.: 426,614

[22] Filed: Apr. 21, 1995

Related U.S. Application Data

[63] Continuation-in-part of Ser. No. 345,142, Nov. 28, 1994, Pat. No. 5,681,308, which is a continuation-in-part of Ser. No. 319,373, Oct. 6, 1994, Pat. No. 5,575,788, which is a continuation-in-part of Ser. No. 286,862, Aug. 4, 1994, Pat. No. 5,558,672, which is a continuation-in-part of Ser. No. 272,162, Jul. 7, 1994, Pat. No. 5,569,241, which is a continuation-in-part of Ser. No. 265,459, Jun. 24, 1994, Pat. No. 5,505,730.

[51] Int. Cl.$^6$ .................................................. A61B 17/36
[52] U.S. Cl. ............................ 606/41; 606/28; 606/194; 607/101; 604/22
[58] Field of Search .................................. 606/27–34, 41, 606/42, 45–50, 191–193, 194; 607/98–102; 604/53, 96–102, 21, 22

[56] References Cited

U.S. PATENT DOCUMENTS 1,620,929  3/1927  Wallerich.
1,827,306  10/1931  Chapman et al..

(List continued on next page.)

OTHER PUBLICATIONS

Singer et al., "Preliminary Clinical Experience With A Thermal Balloon Endometrial Ablation Method To Treat Menorrhagia", *Obstetrics & Gynecology*, vol. 83, No. 5, Part 1, pp. 732–734, May 1994.

Phipps et al., "Treatment of Functional Menorrhagia By Radiofrequency–Induced Thermal Endometrial Ablation", *The Lancet*, United Kingdom, vol. 335, pp. 374–376, Feb. 17, 1990.

Phipps et al., "Experimental and Clinical Studies With Radiofrequency–Induced Thermal Endometrial Ablation for Functional Menorrhagia", *Obstetrics & Gynecology*, United Kingdom, vol. 76, No. 5, Part 1, pp. 876–881, Nov. 1990.

Prior et al., "Treatment of Menorrhagia By Radiofrequency Heating", *Int. J. Hyperthermia*, United Kingdom, vol. 7, No. 1, 22–230, pp. 213–216, 1991.

Mumford et al., "Sterilization Needs In The 1990's: The Case For Quinacrine Nonsurgical Female Sterilization", *American Journal of Obstetrics & Gynecology*, United Kingdom, vol. 167, No. 5, pp. 1203–1207, Nov. 1992.

Neuwirth et al., "The Endometrial Ablator: A New Instrument", *Obstetrics & Gynecology*, vol. 83, No. 5, Part 1, pp. 792–796, May 1994.

*Primary Examiner*—Michael Peffley
*Attorney, Agent, or Firm*—Fliesler, Dubb, Meyer & Lovejoy LLP

[57] ABSTRACT

An endocardial ablation apparatus, for introduction into a heart chamber formed by a wall, is provides. The ablation apparatus includes an inflatable, flexible porous membrane adapted to receive an electrolytic solution, and become inflated to substantially conform an exterior surface of the membrane to the wall of the heart chamber. An inner lumenal member is surrounded by and attached to the membrane. The inner lumenal member includes a lumen that permits blood flow through the inner lumenal member and heart chamber. An introducer catheter introduces the membrane and inner lumenal member into a selected heart chamber. A plurality of RF electrodes define a circuit positioned in the membrane or on an exterior surface of the inner lumenal member. The RF electrodes transfer thermal energy to the electrolytic solution. The electrolytic solution is the electrode that provides ablation of a selected site of the heart chamber. An RF power source is coupled to the RF electrodes. A source of electrolytic solution is coupled to the membrane.

36 Claims, 16 Drawing Sheets

U.S. PATENT DOCUMENTS

| | | |
|---|---|---|
| 3,645,265 | 2/1972 | Majzlin . |
| 3,840,016 | 10/1974 | Lindemann . |
| 3,924,628 | 12/1975 | Droegemueller et al. . |
| 3,948,270 | 4/1976 | Hasson . |
| 4,057,063 | 11/1977 | Gieles et al. . |
| 4,676,258 | 6/1987 | Inokuchi et al. . |
| 4,799,479 | 1/1989 | Spears ........................................ 606/28 |
| 4,865,047 | 9/1989 | Chou et al. . |
| 4,949,718 | 8/1990 | Neuwirth et al. . |
| 4,960,133 | 10/1990 | Hewson . |
| 4,961,435 | 10/1990 | Kitagawa et al. . |
| 4,979,948 | 12/1990 | Geddes et al. . |
| 5,047,028 | 9/1991 | Qian ........................................... 606/49 |
| 5,084,044 | 1/1992 | Quint . |
| 5,151,100 | 9/1992 | Abele et al. ............................... 606/28 |
| 5,156,151 | 10/1992 | Imran ....................................... 128/642 |
| 5,186,181 | 2/1993 | Franconi et al. . |
| 5,188,122 | 2/1993 | Phipps et al. . |
| 5,191,883 | 3/1993 | Lennox et al. ............................. 606/31 |
| 5,228,442 | 7/1993 | Imran . |
| 5,232,444 | 8/1993 | Just et al. ................................. 604/96 |
| 5,236,413 | 8/1993 | Feiring . |
| 5,255,697 | 10/1993 | Grauer . |
| 5,263,493 | 11/1993 | Avitall . |
| 5,277,201 | 1/1994 | Stern ........................................ 607/98 |
| 5,279,299 | 1/1994 | Imran . |
| 5,290,306 | 3/1994 | Trotta et al. .............................. 606/194 |
| 5,311,866 | 5/1994 | Kagan et al. ............................. 607/122 |
| 5,344,402 | 9/1994 | Crocker ..................................... 604/96 |
| 5,505,730 | 4/1996 | Edwards ................................... 606/41 |
| 5,588,432 | 12/1996 | Crowley ................................... 128/660.03 |

ABLATION APPARATUS FOR CARDIAC CHAMBERS

CROSS-REFERENCE TO RELATED APPLICATIONS

This application is a continuation-in-part of U.S. patent application Ser. No. 08/345,142 entitled "Ablation Apparatus For Cardiac Chambers" by Edwards filed Nov. 28, 1994 now U.S. Pat. No. 5,681,308, which is a continuation-in-part of U.S. patent application Ser. No. 08/319,373 entitled "Thin Layer Ablation Apparatus" by Baker et al, filed Oct. 6, 1994 now U.S. Pat. No. 5,575,788, which is a continuation-in-part of U.S. patent application Ser. No. 08/286,862 entitled "Thin Layer Ablation Apparatus" by Edwards et al, filed Aug. 4, 1994 now U.S. Pat. No. 5,558,672, which is a continuation-in-part of U.S. patent application Ser. No. 08/272,162 entitled "Thin Layer Ablation Apparatus" by Edwards, et al, filed Jul. 7, 1994 now U.S. Pat. No. 5,569,241, which is a continuation-in-part of U.S. patent application Ser. No. 08/265,459 entitled "Thin Layer Ablation Apparatus" by Edwards filed Jun. 24, 1994 now U.S. Pat. No. 5,505,730, all of which are incorporated by reference.

BACKGROUND OF THE INVENTION

1. Field of the Invention

This invention relates to an ablation and mapping apparatus for use in the field of cardiac arrhythmia, and more particularly to an apparatus for treating atrial fibrillation.

2. Description of Related Art

The Sino Atrial ("SA") node provides impulses which control the normal rhythmic contractions of the heart atria and the ventricles. This involves the transmission of the normal cardiac conduction pathways in the atria and the ventricles, which cause the heart to contract and relax in an orderly sequence at a rate set by the SA node.

A depolarization impulse begins with the SA node and spreads as an electrical wave in the SA node in the right atrium to the left atrium and down toward the lower chambers of the heart. At the junction of the atria and the ventricles there is another node known as the atrioventricular (AV) node. The impulse is conducted through the AV node in a slower fashion so as to coordinate the mechanical function of the atria and ventricles. The impulse continues to a common pathway, known as the bundle of HIS between the right and left ventricles, and then into the Purkinje system and into multiple paths, the right and left bundle branches, each bundle branch supplying one ventricle. Each bundle branch divides into an extensive network of finer paths of conducting tissue, which spread from the inner to the outer surfaces of the heart and are referred to as the Purkinje fibers. These fibers conduct the depolarization impulse into all portions of the ventricular myocardium.

As long as this depolarization impulse system is intact impulses are transmitted normally and the normal sinos rhythm is maintained. Sometimes there are variations from the normal rhythm of the heart beat which are manifested as abnormal spontaneous contractions or as rapid sequences of impulses that dangerously speed the heart rhythm (tachycardia), or the heart rate may slow below normal (bradycardia) which can also compromise the individual. These abnormalities are clinically referred to as arrhythmias and they can cause numerous unwanted and potentially dangerous complications for patients.

The arrhythmogenic focus that initiates tachyarrhythmias is most often located in the endocardium or interior surface of the heart. Since the heart muscle contractions result from the progression of an excitation wave of electrical impulses. The location of an arrhythmogenic focus is accomplished by identifying the point from where the abnormal excitation wave originates by the use of intra-cardiac mapping.

Ventricular tachycardia (VT) and other ventricular arrhythmias, have been treated with a number of drugs such as lidocaine, quinidine, aminodrone and procainamide. Beta blocking drugs have also been used. Certain surgical procedures have been used to ablate the foci of arrhythmias in either the atria or the ventricles, when drug therapy has been ineffective in preventing tacharrhythmias.

One surgical approach involves a thoracotomy with an incision through the pericardium and heart muscle. The arrhythmogenic focus is located, frozen or surgically removed. The surgical procedure utilizes either a hand held electrical mapping probe or a computerized array of electrodes that are placed on the endocardium (inner wall) or the epicardium (outside wall) of the heart, which acquire electrical activation data to identify the site of origin of the arrhythmia. Less traumatic solutions have been developed.

Various types of intervention catheters have been developed and used for diagnosis and treatment of a number of cardiac abnormalities to avoid the trauma of open heart surgery, which requires a prolonged period of hospitalization and recuperation. In percutaneous catheter procedures, a catheter with recording electrodes is positioned in the heart under fluoroscopic guidance. Following acquisition of the electrical activation data, ablation energy is then delivered via the catheters either in a radiology suite or in the cardiac catheterization lab.

Catheters have been proposed to map arrhythmogenic foci, as disclosed in U.S. Pat. Nos.: 5,156,151; 5,255,697; 5,228,442; 5,263,493 and 5,279,299. However, these catheters fail to provide for the identification, isolation and quick instruction to treat an arrhythmogenic focus. The successful use of radio frequency (RF) energy to eliminate VT requires an accurate "pace map" of the earliest local activation from a catheter in contact with the endocardium.

For patients with coronary artery disease, failure to eliminate VT using RF energy delivered through a catheter has been hypothesized to be due to the small size and shallow depth of the lesion created by RF energy, preventing it from reaching subendocardial (or deeper) regions of the heart. Additional contributing factors may also include inaccurate mapping in scarred ventricles or a location of the arrhythmogenic focus at sites below the surface of the endocardium. Direct current and RF energy have been utilized in these attempts.

There has been successful elimination of idiopathic, usually in the right ventricular VT, in patients without structural heart disease with direct current countershocks, however, complications such as trauma and risk of ventricular perforation associated with direct current countershocks make this technique less desirable unless very low energies are used.

It would be desirable to provide an ablation apparatus which is inserted into a heart chamber, such as an atrium which expands from a folded configuration, identifies and localizes the arrhythmogenic focus and then quickly instructs an energy delivery source to treat the arrhythmogenic focus. There is a need to treat arrhythmogenic foci deep in the endocardium with a system that can be in intimate contact with the irregular surface of the endocardium. It would be desirable to provide a cardiac ablation apparatus which provides ablation depths suitable to effectively treat arrhythmogenic foci (transmurally across the muscular wall of the heart), including an ability to reach the subendocardial or deeper region of the heart.

SUMMARY OF THE INVENTION

Accordingly, an object of the present invention is to provide a cardiac ablation apparatus which provides a plurality of RF electrode segments for the controlled ablation of the endocardium and transmural regions of the heart muscle.

Another object of the present invention is to provide a cardiac ablation apparatus which provides an expandable member that can simultaneously address the entire surface of a chamber and surrounds an inner lumenal member which provides blood flow through an interior lumen of the inner lumenal member.

A further object of the present invention is to provide a cardiac ablation apparatus which positions the RF electrodes on an exterior surface of an inner lumenal member that uses an electrolytic solution to effectively ablate selected zones of tissue, without intimate contact between the RF electrodes and the heart chamber.

Yet another object of the present invention is to provide a cardiac ablation apparatus which provides an electrolytic solution delivered through the microporous membrane to the endocardium that acts as a part of the RF circuit.

Another object of the invention is to provide a cardiac ablation apparatus which includes a microporous membrane, inner lumenal member and electrodes positioned on an outside surface of the inner lumenal member.

Still another object of the invention is to provide a cardiac ablation apparatus which includes a microporous membrane, inner lumenal member, RF electrodes positioned on at outside surface of the inner lumenal member, and a plurality of recording electrodes positioned on an exterior surface of the membrane.

A further object of the invention is to provide a cardiac ablation apparatus which provides a flexible circuit of RF electrodes with segments that can be multiplexed to provide tailored areas of ablation.

Yet another object of the present invention is to provide a cardiac ablation and mapping apparatus that includes a microporous membrane in direct contact with the endocardium, and resources to map the heart in order to determine the origin of the arrhythmia by identifying the location of endocardial activation and then to ablate an arrhythmogenic focus with an electrolytic solution.

These and other objects of the invention are provided in an endocardial mapping and ablation apparatus that is introduced into a heart chamber, particularly an atrium, to treat atrial fibrillation. An inflatable flexible porous membrane is adapted to receive an electrolytic solution and become inflated to substantially conform an exterior surface of the membrane to the wall of the heart chamber. An inner lumenal member is surrounded by and attached to the membrane. The inner lumenal member includes a lumen that permits blood flow through the inner lumenal member and the heart chamber. An introducer catheter introduces the membrane and inner lumenal member into a selected heart chamber. A plurality of RF electrodes define a circuit positioned in the membrane or on an exterior surface of the inner lumenal member. The RF electrodes transfer thermal energy to the electrolytic solution. The electrolytic solution is the electrodes provides an ablation of a selected site of the heart chamber. An RF power source is coupled to the RF electrodes. A source of electrolytic solution is coupled to the membrane.

The ablation apparatus further includes electrical resources for acquiring electrical data from the heart and providing electrical function feedback to the RF generator, which then supplies a therapeutic output of RF energy to the plurality of RF electrodes in response to the electrical data with a transfer of energy from the RF electrodes to an electrolyte solution in close proximity to the RF electrodes. The inner lumenal member structure includes the lumen that permits blood to flow through the right atrium at the inlet of the superior vena cava, the inlet of the inferior vena cava and at the tricuspid annulus. Blood does not flow from the lumen into the membrane. A ground pad can be attached to an exterior surface of a patient for monopolar use or the apparatus can be operated in a bipolar mode.

Attachment members are positioned on a catheter distal end and attach to the membrane or inner lumenal member. After the procedure is completed, the membrane and inner lumenal member are rolled around the catheter distal end and removed from the heart chamber.

An exterior surface of the membrane, e.g., the surface located adjacent to the endocardium, can be coated with an anti-coagulating material.

The RF electrodes can also be positioned in an interior of the membrane. In this embodiment, the RF electrodes are spaced apart from the membrane's exterior surface so that there is no direct contact between the RF electrodes and the endocardium. Instead the actual electrode which transmits ablative energy to the selected endocardium site is the electrolytic solution.

The RF electrodes can form a flexible circuit with associated thermocouples. Individual RF electrodes are treated as segments in the flexible circuit. These segments can be multiplexed by energizing different RF electrodes. Ablation of the endocardium can be at a desired level, including the subendocardium and deeper, based on the detected characteristic of the arrhythmogenic focus.

The present invention provides mapping and detection of the arrhythmogenic foci, ablation at the appropriate depth and subsequent re-mapping, and allows the blood to flow through the heart chamber is substantially uninterrupted. The RF ablation energy is delivered from the RF electrodes to surrounding electrolytic solution. The heated electrolytic solution transfers thermal energy from the RF electrodes and creates an ablation at selected endocardium sites

DETAILED DESCRIPTION

The present invention provides a cardiac ablation and mapping system 10, which includes a cardiac ablation and mapping apparatus. Cardiac ablation and mapping apparatus includes a microporous membrane, surrounding an inner lumenal member, a plurality of RF electrodes that are positioned between an exterior surface of the inner lumenal member and an exterior surface of the microporous membrane, and a plurality of recording electrodes positioned on the exterior surface of the membrane. The membrane is made of a material that permits it to closely conform to the wall of the heart and expand by the introduction of fluid, such as an electrolytic solution. The inner lumenal member can be a balloon or other suitable mechanical apparatus, which permits blood to flow uninterrupted through a lumen of the inner lumenal member when it is positioned in the heart chamber but does not permit blood to pass through the lumen and into the microporous membrane.

The ablation apparatus is introduced into a selected heart chamber in a non-expanded configuration, in a folded or rolled configuration around a distal end of a catheter. Once the ablation apparatus is positioned in the desired heart chamber it is expanded. The expansion occurs when electrolytic solution is introduced into the membrane. The RF electrodes are not in direct physical contact with the heart wall. Recording electrodes and electrical resources are included to map the heart to acquire electrical activation data to seek the origin of the arrhythmia, provide early local endocardial activation, electrical function feedback to an RF generator, and then provide a therapeutic output via the RF electrodes and surrounding electrolytic solution to ablate an arrhythmogenic focus.

An uneven penetration of energy to the endocardium can be produced. This is particularly desired in the MAZE procedure. Across the endocardium, tissue is ablated in a maze like pattern, eliminating reentry pathways.

Figure 1:
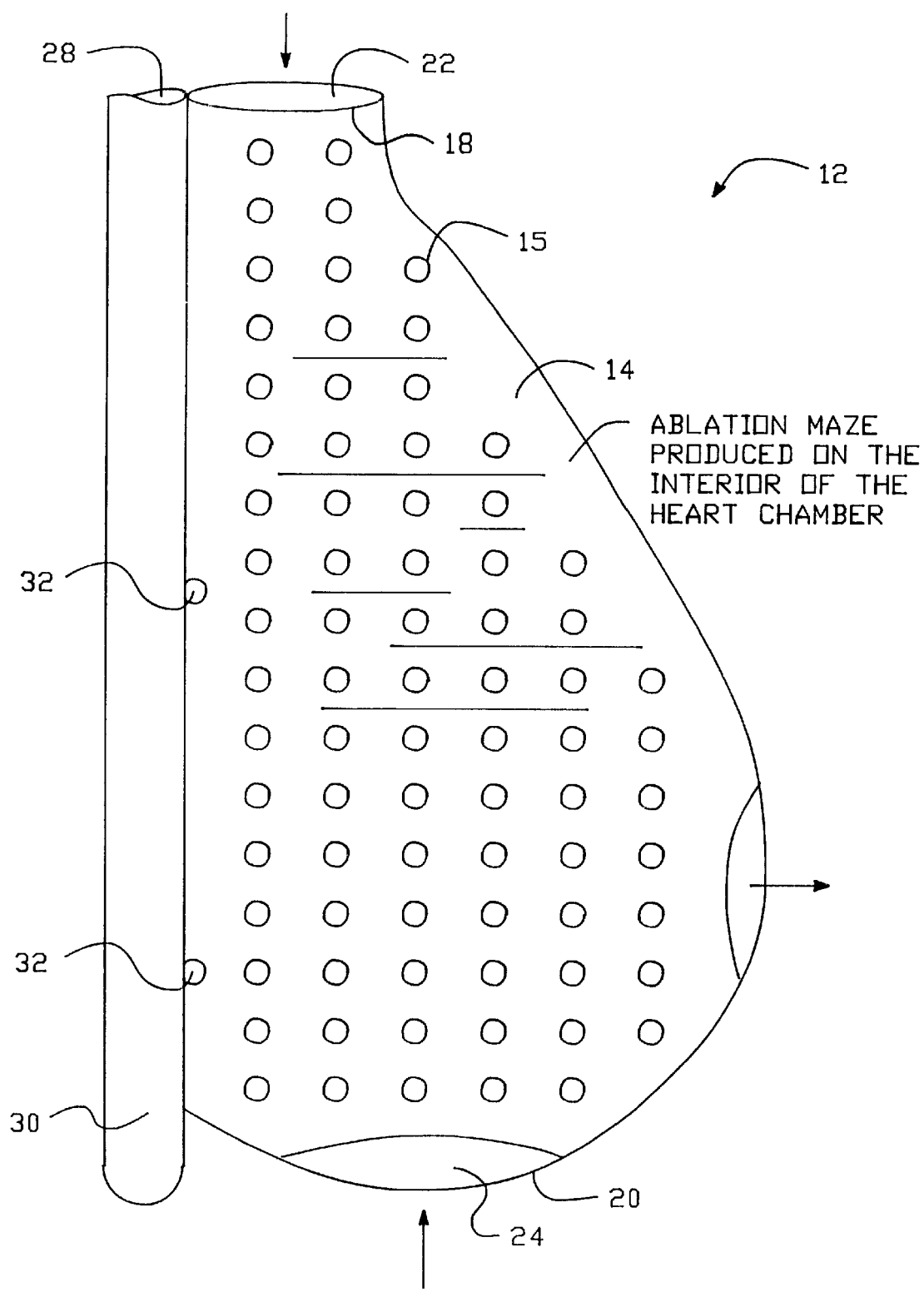
FIG. 1 is a perspective view of the cardiac ablation and mapping apparatus of the invention illustrating the creation of ablation zones suitable for the "MAZE" procedure. An ablation MAZE is illustrated.
Figures 2, 3:
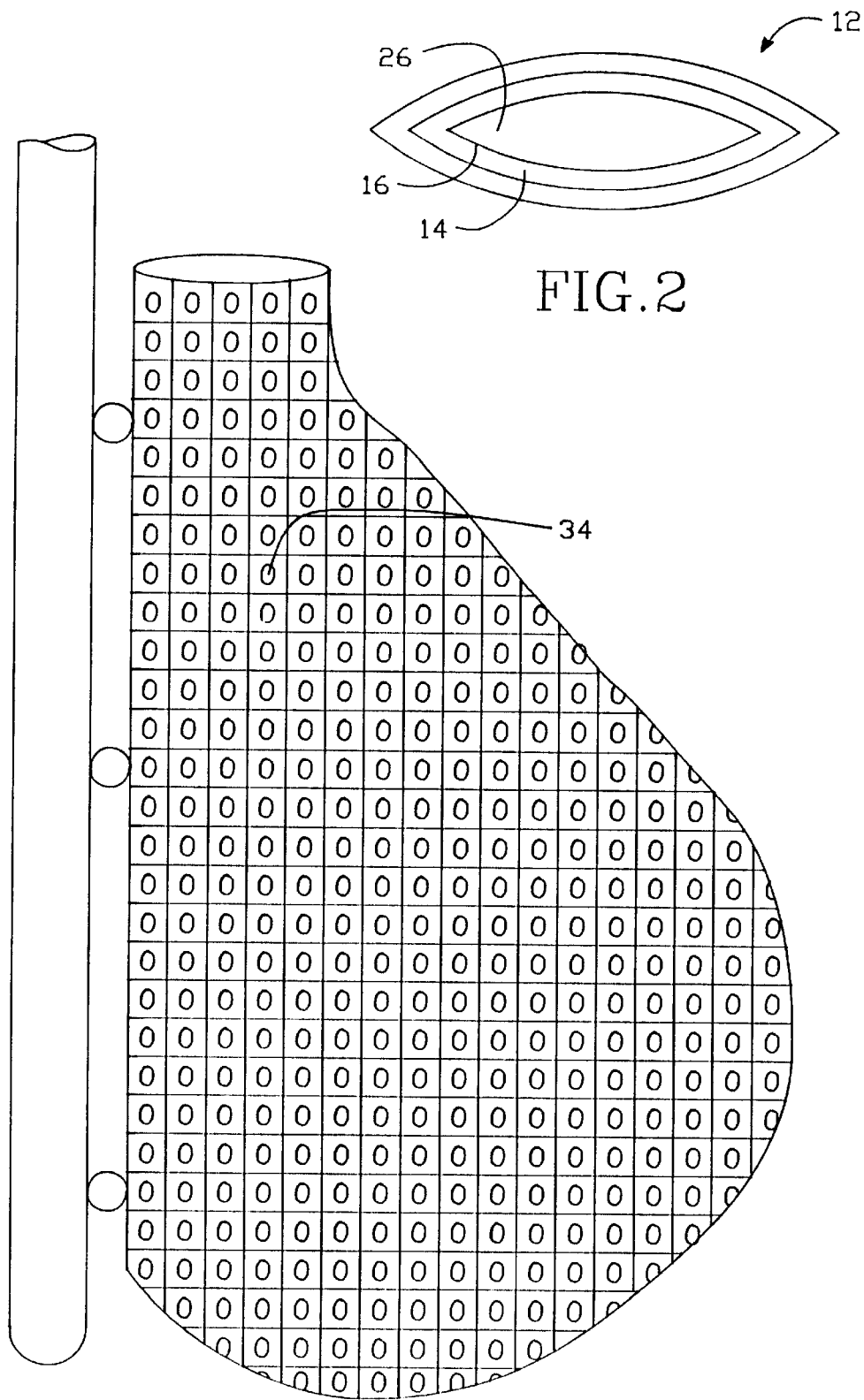
FIG. 2 is a cross-sectional view of the ablation and mapping apparatus of FIG. 1.
FIG. 3 is a perspective view of an exterior wall of the inner lumenal member of the invention with the electrodes positioned on the exterior wall.

Referring now to FIGS. 1 and 2, cardiac ablation and mapping system 10, particularly suitable for the right atrium includes a cardiac ablation and mapping apparatus 12. Ablation apparatus 12 includes a porous membrane 14 which surrounds an inner lumenal member 16. Inner lumenal member 16 provides a separation of membrane 14 and the electrolytic solution from the flow of blood through a lumen formed in the inner lumenal member 16, as more fully explained hereafter. Membrane 14 can be of the microporous type and be made of Mylar, expanded PFT such as Gortex available from Gore Company and the like. Membrane 14 is relatively strong and sufficiently heat resistant for the amount of thermal energy that is supplied to the endocardium. The flow rate of electrolytic solution through membrane 14 is determined by, (i) the porosity of membrane 14 and (ii) the introduction rate of the electrolytic solution to membrane 14. A plurality of recording electrodes 15 are positioned on an exterior surface of membrane 14. Recording electrodes 15 can be MAP monophasic action potential electrodes, comprised of a silver or a silver chloride matrix which can be either deposited on the surface of membrane 14 or more conventional intracardial electrode compositions. Alternatively, recording electrodes 15 can be independent electrodes that are placed on the outside surface of membrane 14.

Membrane 14 substantially surrounds inner lumenal member 16. Inner lumenal member 16 includes a sealed proximal end 18 and a sealed distal end 20. It will be appreciated that ends 18 and 20 can be configured to be positioned next to the associated venous inlet or valve, to more readily orient ablation apparatus 12 and position it properly in the left or right atrium. Ends 18 and 20 are sealed but include an aperture 22 and 24 respectively, formed therein, defining a central lumen 26 which extends in a general longitudinal direction through inner lumenal member 16 permitting blood to flow through inner lumenal member 16 and the heart chamber. Inner lumenal member 16 is attached to membrane 14 and is expanded to a non-distensible state when membrane 14 is inflated with solution.

A catheter 28, with a distal end 30, may be attached to membrane 14 or inner lumenal member 16 with attachment devices including, but not limited to hooks, loops and the like. Catheter 28 may be a combination of a latex/silicon rubber composite that has a non-pliable, non-flexible, inner sleeve or glove. Catheter 28 can also serve as a "spine" for ablation apparatus 12. Membrane 14 and inner lumenal member 16 are initially in a folded or rolled type of basket, non-expanded configuration, and wound around catheter distal end 30. Catheter distal end 30 can be introduced into the right atrium through, (i) the subclavian vein, requiring a catheter 28 length of about 30 to 40 cm, (ii) the internal jugular, requiring a catheter 28 length of about 30 to 40 cm or (iii) the femoral artery, requiring a catheter 28 length of about 110 cm.

Generally, cardiac ablation and mapping apparatus 12 can be a monopolar or bipolar RF electrode system that is capable of expanding so that membrane 14 becomes expanded within the heart chamber, and RF and thermal energy are delivered by electrolytic solution to the wall of the heart through membrane 14. RF and thermal energy are passed by the electrolytic solution through the endocardium and subendocardium or deeper, for a time period sufficient to achieve a desired level of ablation at an arrhythmogenic focus. It can be used in the "MAZE" procedure which does not address a particular focus but creates a condition where reentry is inhibited.

In a monopolar mode, an RF current flows through body tissue from a return electrode in the form of a conductive pad applied to the patient's outer skin. Maximum heating occurs where the current density is the greatest. The electric current flowing through the endocardium causes heating due to the resistance of the tissue. Intravascular or cardial ablation can be accomplished as a relatively simple medical procedure.

Membrane 14 conforms tightly with the interior of the heart so that substantially all of the heart wall is in contact with the exterior surface of membrane 14. Membrane 14 fits substantially into the entire heart chamber and does not have to be moved about the heart to complete the treatment. Membrane 14 is made of a material that suitably conforms to a surface to be ablated and can have a thickness in the range of about 0.01 to 2.0 cm. Fluid flow can be continuous or non-continuous. The electrolytic solution delivered to membrane 14 can be heated, as more fully explained below.

Referring now to FIG. 3, a plurality of RF electrodes 34 are positioned on an exterior surface of inner lumenal member 16. There is no direct contact or RF electrodes 34 to the endocardium.

Figure 4:
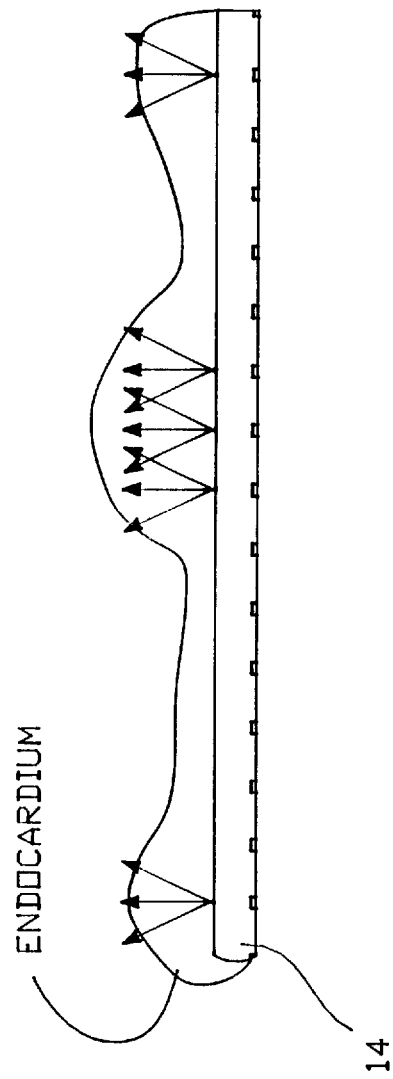
FIG. 4 is an illustration of an ablation device with direct ablation of the endocardium by an electrolytic solution which has been in thermal contact with the RF electrodes.

An electrolytic solution, including but not limited to saline, flows through membrane 14 and comes in thermal contact with RF electrodes 34. Thermal energy is then delivered, via the electrolytic solution, to the endocardium. Thus, the actual electrode for thermal treatment purposes is not RF electrodes 34 but is the electrolytic solution which receives thermal energy from RF electrodes 34, as illustrated in FIG. 4.

Figure 5:
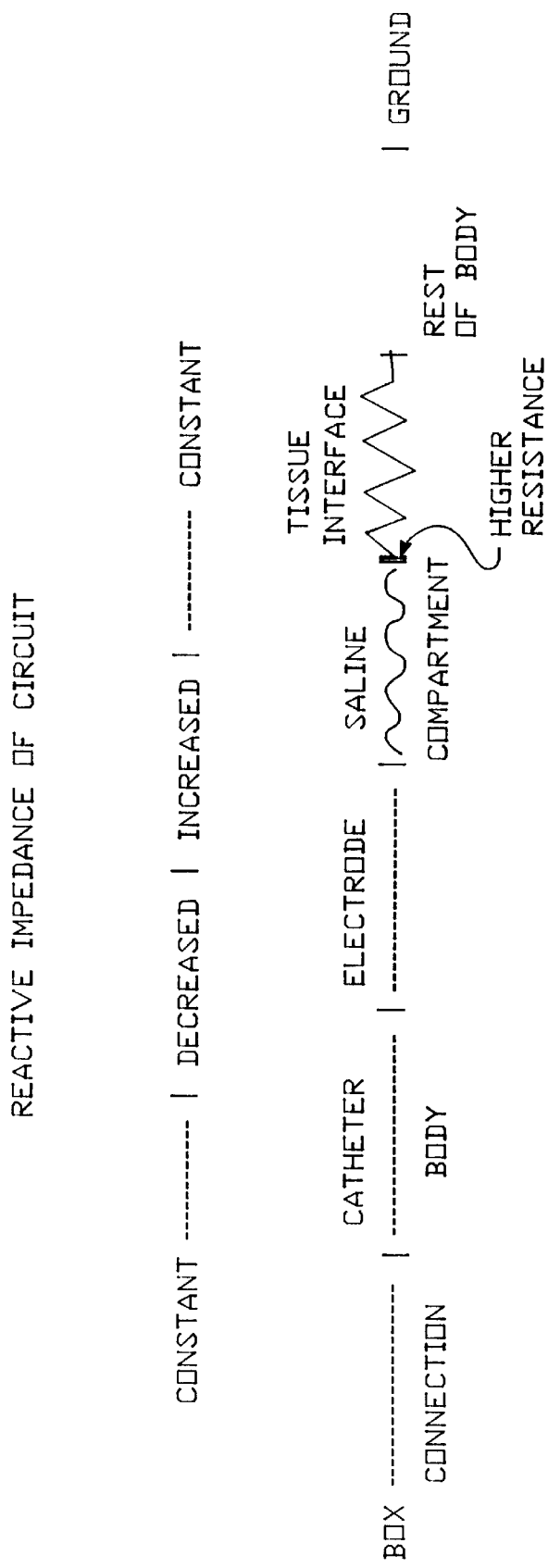
FIG. 5 is a diagram of the relative impedance of the circuit of the present invention.

The impedance of the circuit of the present invention is illustrated in FIG. 5. There is a constant impedance from the RF energy source to RF electrodes 34. When electrolytic solution is placed in intimate contact with RF electrodes 34 there is a decrease in impedance. At the tissue interface the impedance increases because there is higher resistance. Through the rest of the body, and to ground, the impedance is then constant.

Figure 6:
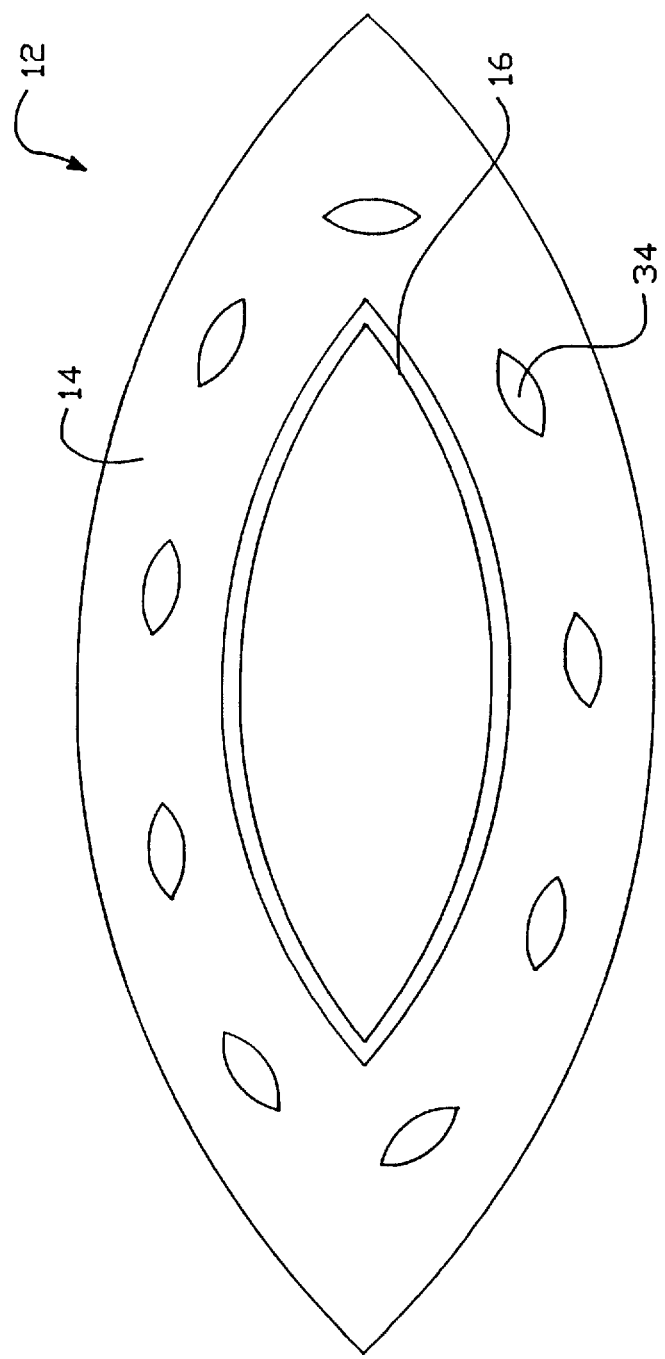
FIG. 6 is a cross-sectional view of the ablation and mapping apparatus of the invention with the RF electrodes positioned within the membrane.

RF electrodes 34 can also be positioned in membrane 14, as shown in FIG. 6. Again, energy transfer occurs through the electrolytic solution which is in contact with RF electrodes 34. The electrolytic solution serves as a thermal transfer electrode and there is no direct contact of RF electrodes 34 to the endocardium.

Figure 7:
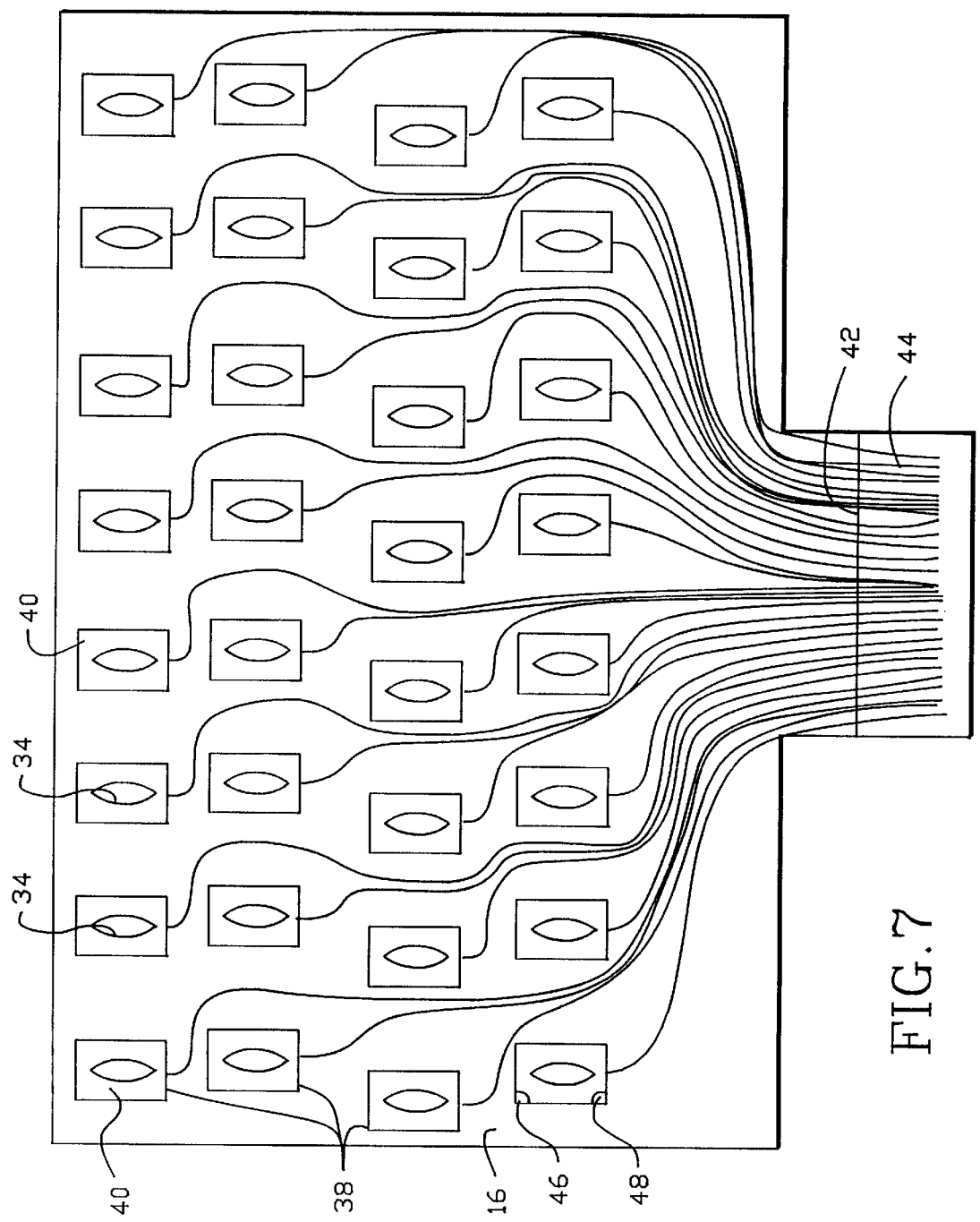
FIG. 7 is a perspective view of a circuit on the exterior of the inner lumenal member with RF electrode segments.

Referring now to FIG. 7, a circuit 38 which can be flexible and made of individual circuit segments 40, can be a printed circuit that is deposited, etched or painted with a conductive ink on inner lumenal member 16, or on a separate support member. Each circuit segment 40 or RF electrode 34 connects to a separate feedwire 42, with all of the wires going to a ribbon connector 44. Feedwires 42 are insulated. Each RF electrode 34 or circuit segment 40, is wired with a constantan wire in order to receive RF energy from an RF energy source. A copper wire is connected to each constantan wire. This results in the formation of a T type thermocouple "TC".

RF power is applied to the desired RF electrode 34 delivering thermal energy only to the electrolytic solution in proximity with the desired RF electrode, which then transfers thermal energy to a selected site of the endocardium. The use of different RF electrodes 34 permits circuit 38 to be multiplexed. The size of individual RF electrodes 34 and circuit segments 40 is designed to provide the correct current density. RF power can be sequentially supplied to each RF electrode 34 and feedwire 42 in ribbon connector 44, or it can be applied to only certain selected feedwires 42. Enabling only selected RF electrodes 34 to deliver RF and thermal energy individually to the electrolytic solution and then to the endocardium.

One or more impedance monitors 46 can be used to confirm, before an ablation event, so that good coupling of energy is achieved. Also, included is one or more thermal sensors 48. Thermal sensors 48 are conventional thermistors or thermocouples and can be positioned on RF electrodes 34 or segments 40.

Figure 8:
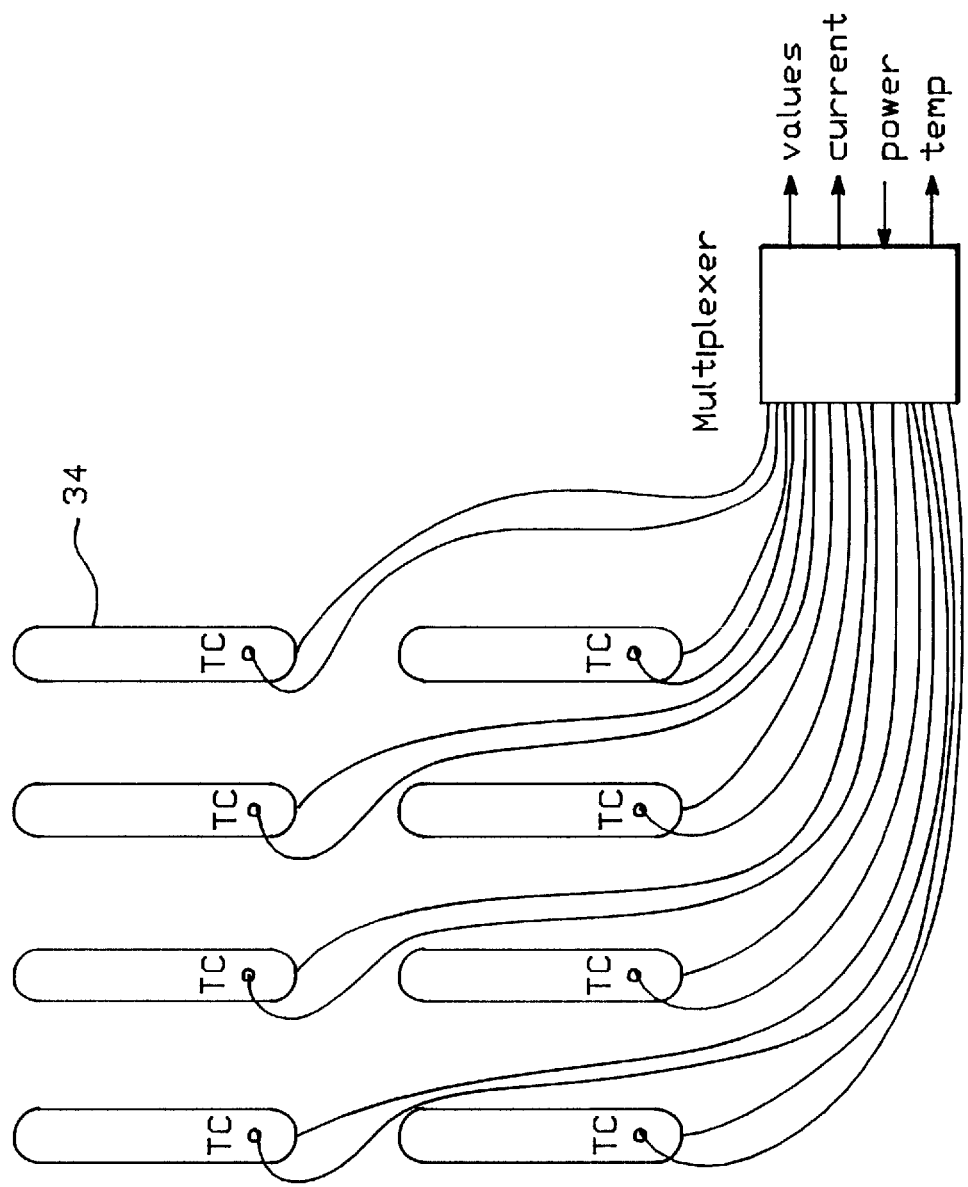
FIG. 8 is an illustration of a plurality of RF electrodes suitable for use with the present invention.

With reference now to FIG. 8, individual RF electrodes 34 can be used and multiplexed in either mono-polar or bi-polar configurations. Circuit segments 40 and RF electrodes 34 are capable of multiplexing so that only one delivers RF energy to surrounding electrolytic solution at a particular time period. RF energy is selectively delivered so that the amount of energy delivered by each circuit segment 40 or RF electrode 34 can vary depending on the detected characteristics of endocardium at a particular area.

Figure 9:
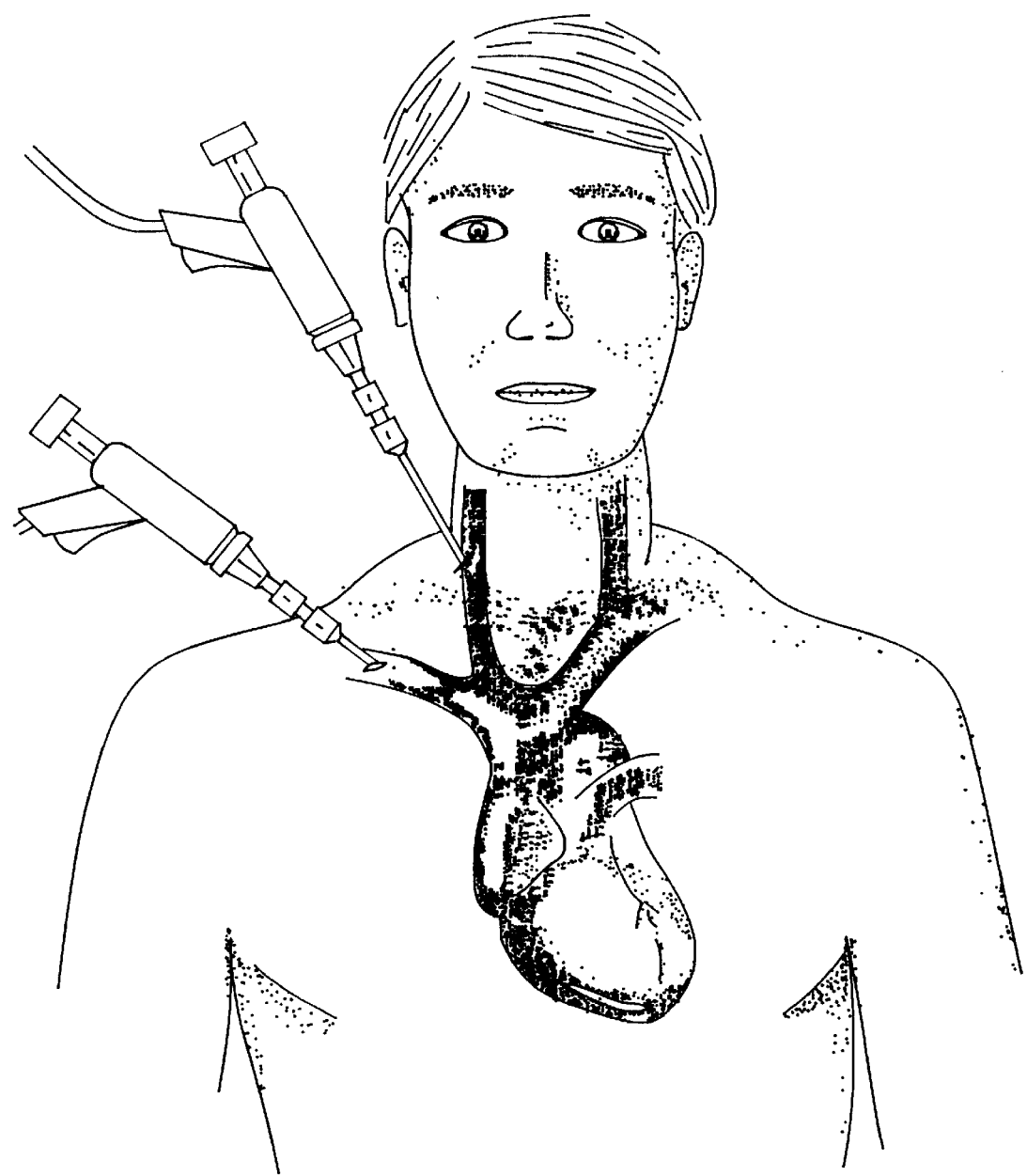
FIG. 9 illustrates the introduction of the ablation apparatus into the desired vein.
Figure 10:
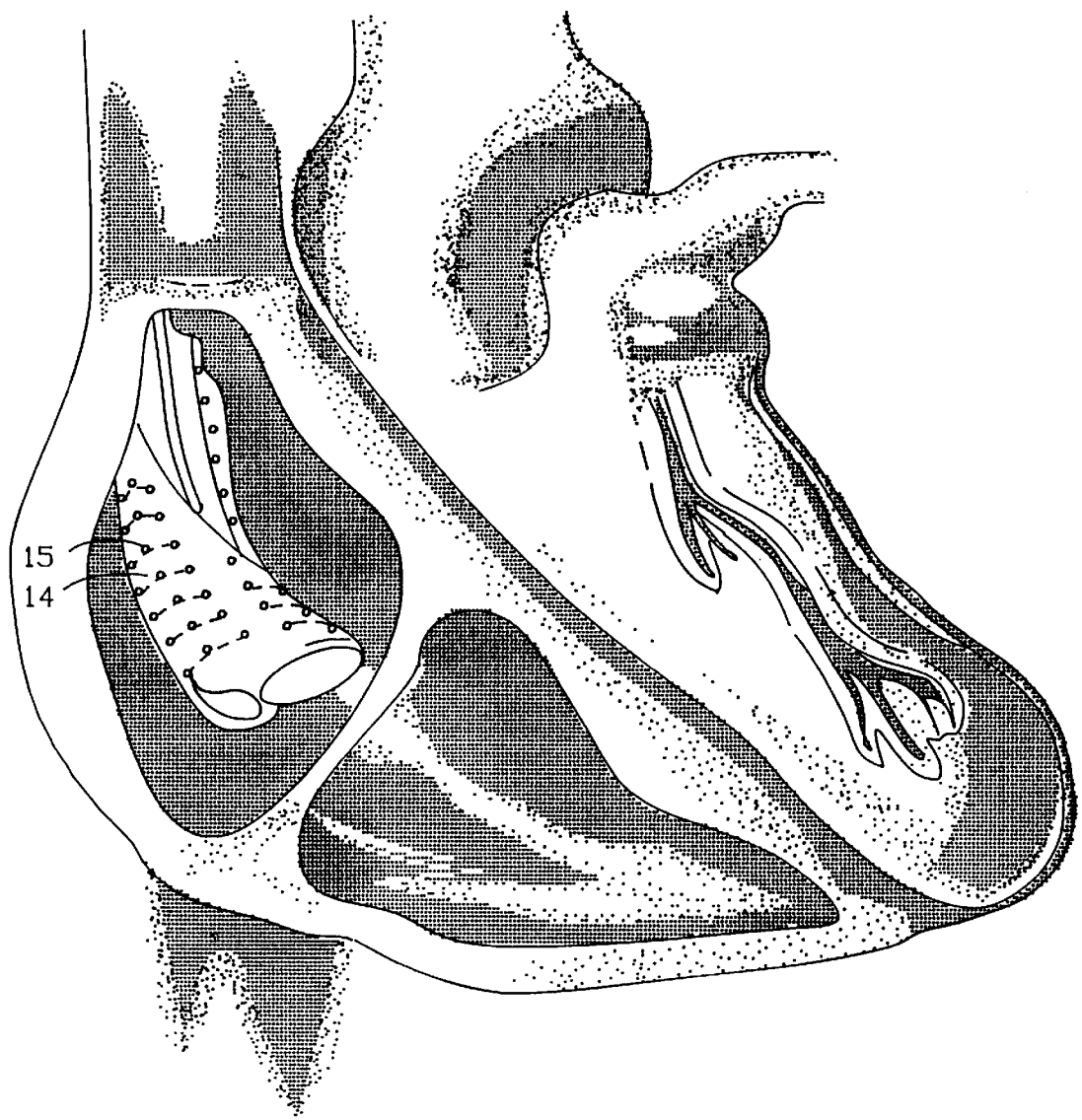
FIG. 10 is a cross-sectional view of the ablation apparatus being positioned in the right atrium before it is expanded.
Figure 11:
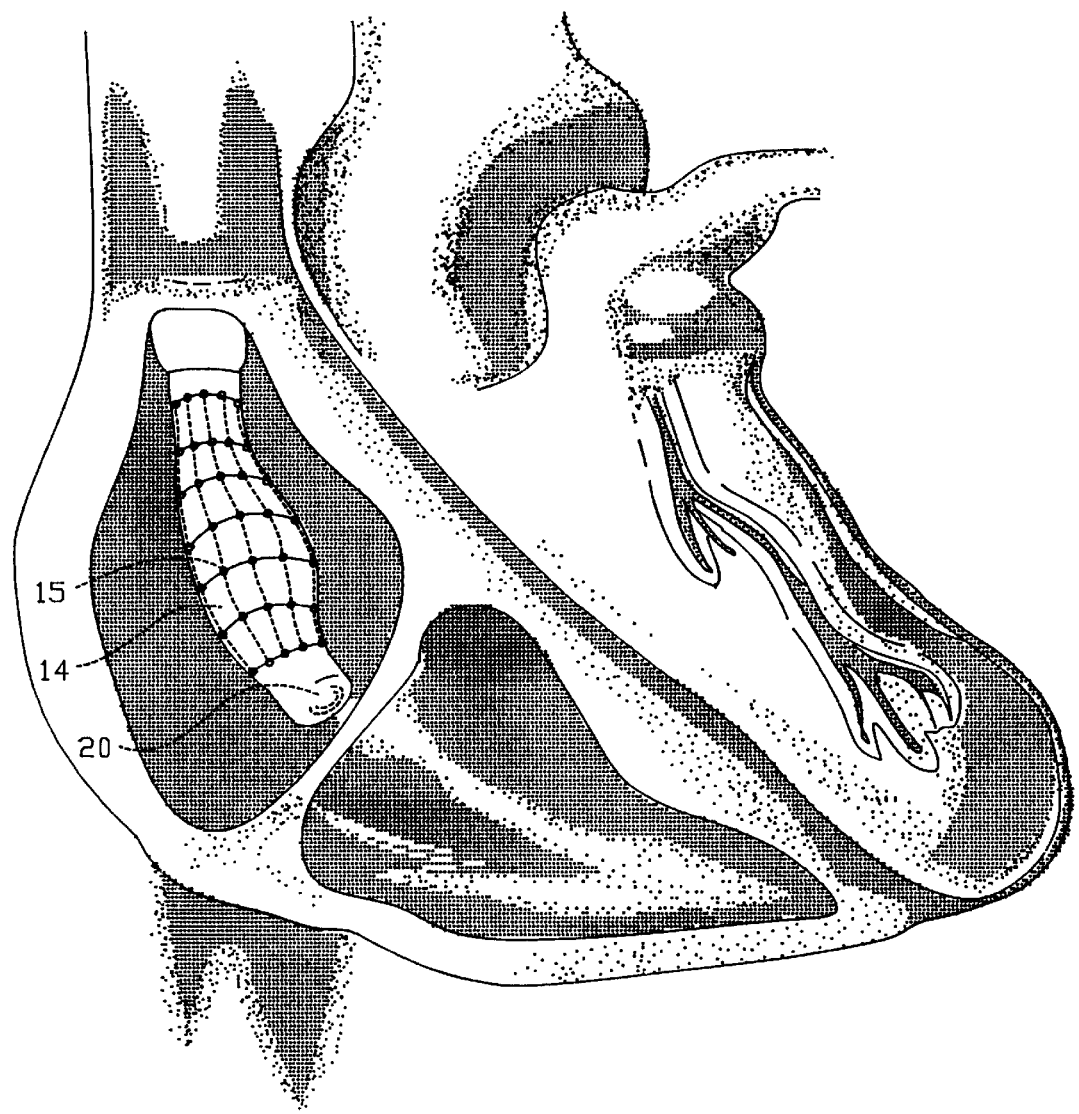
FIG. 11 is a cross-sectional view of the ablation apparatus being positioned in the right atrium, which illustrates the seating of the apparatus in the atrium.
Figure 12:
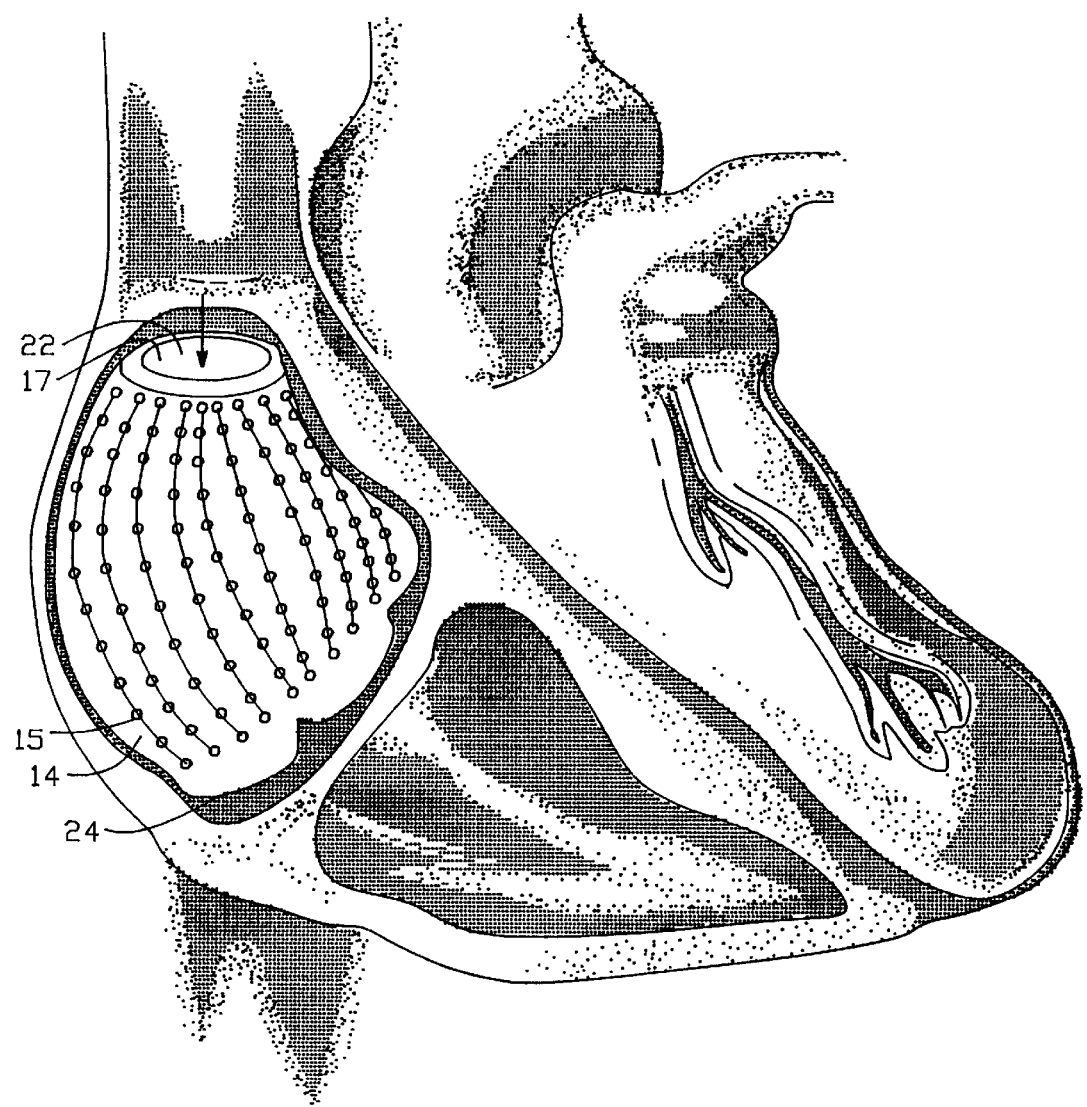
FIG. 12 illustrates an expanded ablation apparatus positioned in the right atrium.

In FIG. 9, ablation apparatus 12 is shown as being introduced through the jugular or subclavian veins. In FIG. 10, ablation recording electrodes 15 are shown as being positioned on an exterior surface of membrane 14 in a folded or rolled configuration as ablation apparatus 12 is introduced into the right atrium. Ablation apparatus 12 begins to unfold in FIG. 11, with end 20 seeking its position in the tricuspid annulus. In FIG. 12, ablation apparatus 12 has become expanded so that membrane 14, and recording electrodes 15, are in a contacting relationship with the wall of the right atrium. Blood flow is not impeded and flows through lumen 26 of inner lumenal member 16 through apertures 22 and 24 respectively. With ablation apparatus 12 in its expanded state and positioned in an atrium there is constrained contraction of the atrium. Mapping and analysis of the heart chamber activation, with the use of recording electrodes 15, occurs substantially at once and can occur within less than ten heart beats or sufficiently long enough to obtain the required intracavitary map.

Figure 13:
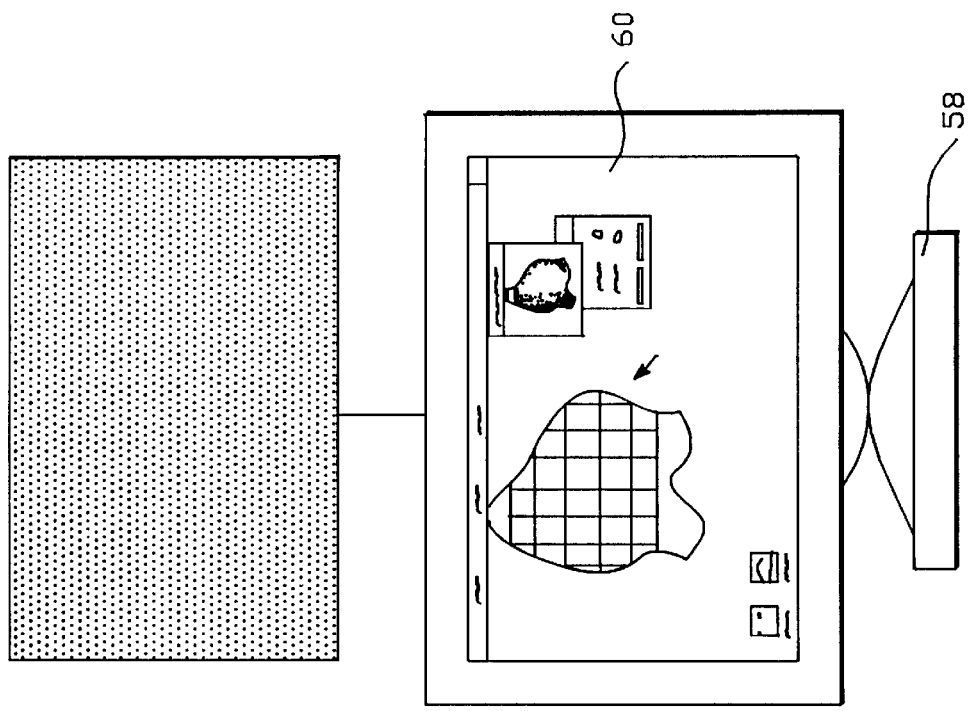
FIG. 13 illustrates the output from the ablation apparatus on a display screen.
Figure 13:
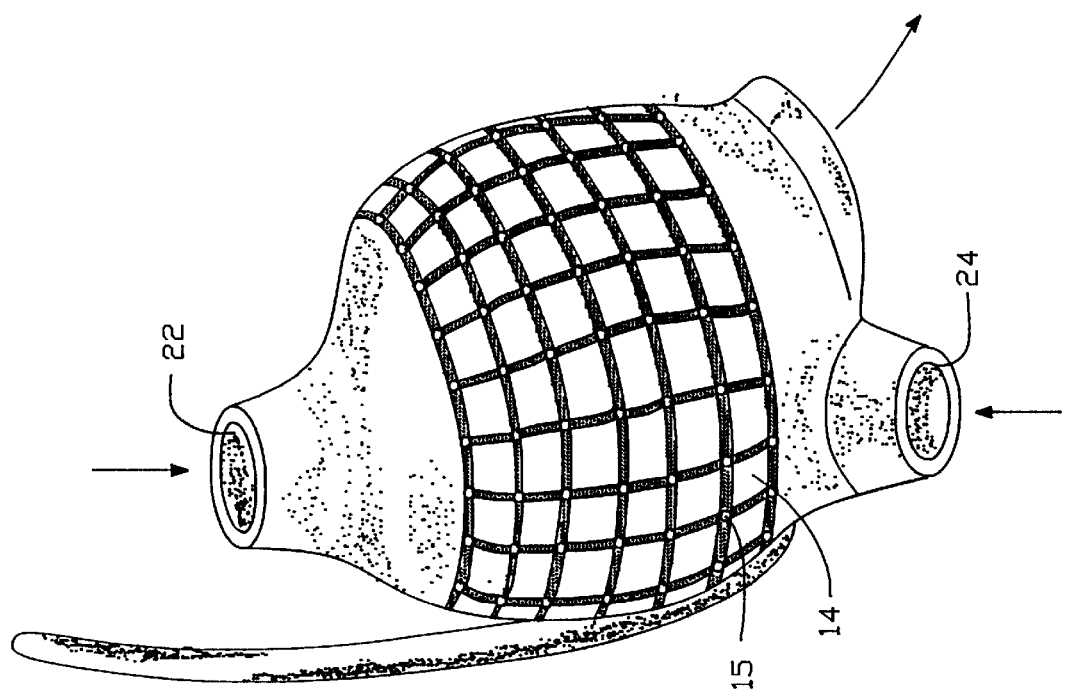

FIG. 13, shows, uninterrupted blood flow through the superior vena cava, inferior vena cava and the tricuspid value. The electrical data output and intracavitary map can be presented on a viewing screen.

Figure 14:
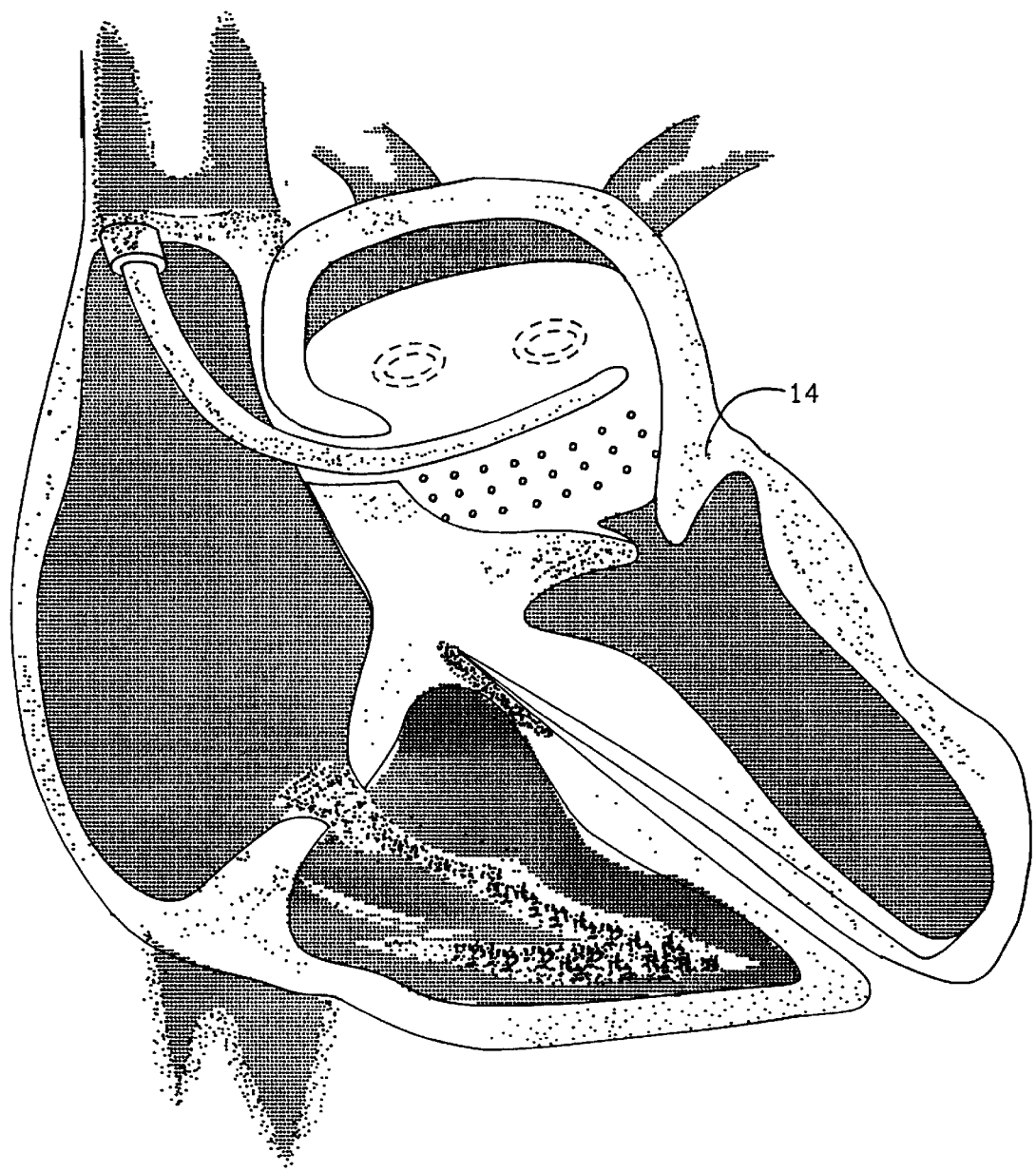
FIG. 14 illustrates placement of the ablation apparatus in the left atrium.

In FIG. 14, ablation apparatus 12 is introduced into the left atrium . There are four pulmonary veins. Ablation apparatus 12 covers only two of the pulmonary veins at one time and the mitral valve. Therefore, ablation apparatus 12 is flipped over in the right atrium to cover the other two pulmonary veins and mitral valve. Ablation apparatus 12 is introduced into the left atrium either with a puncture type of structure across the septal wall or through a patent ductus.

Figure 15:
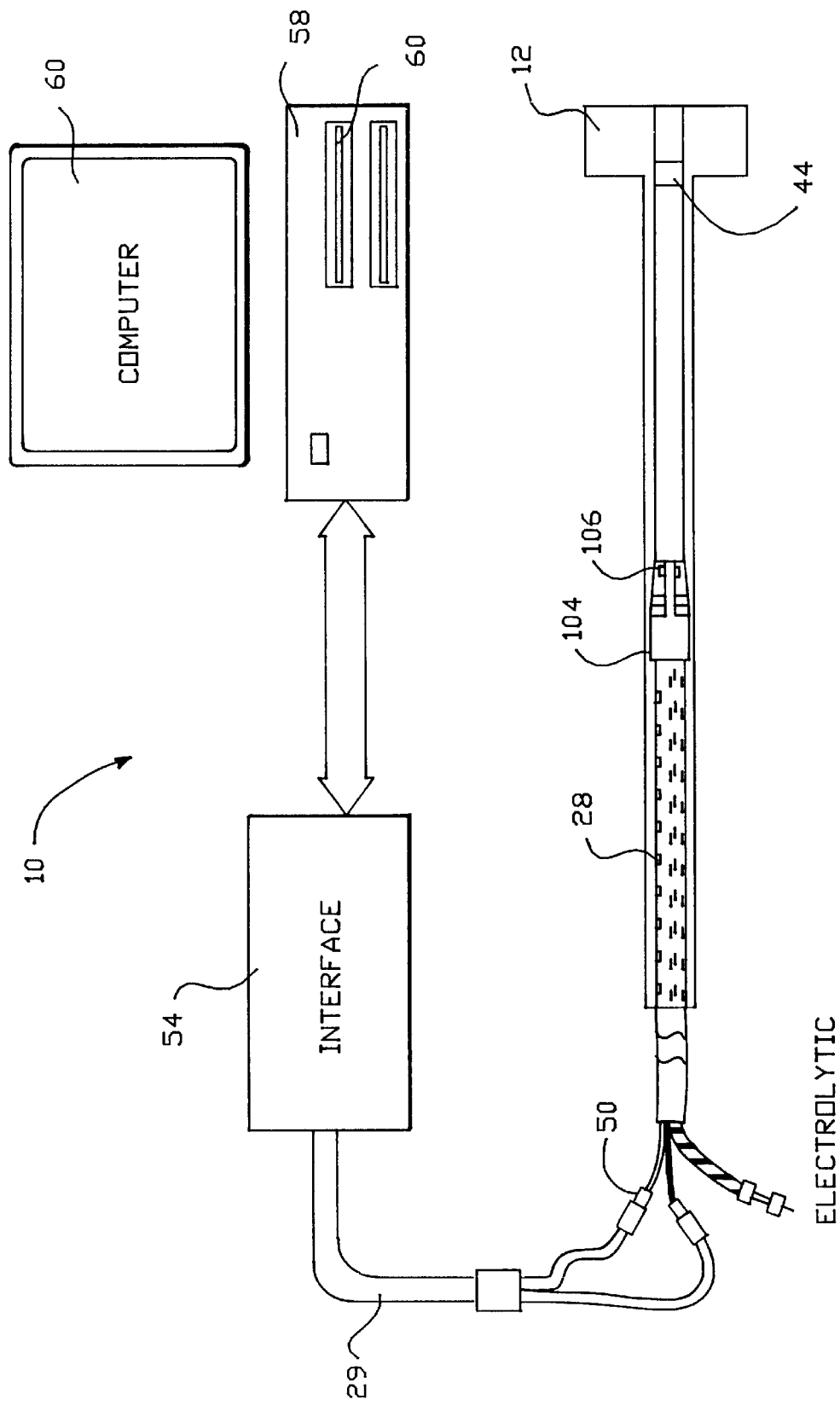
FIG. 15 is schematic diagram of the cardiac ablation and mapping system of the invention.

Referring now to FIG. 15, endocardial ablation and mapping system 10 is illustrated. A high voltage connector 50 and a signal connector are connected to the electrodes (not shown) and form part of catheter 28. A cable 29 is connected to an interface module 54 which supplies and receives signals to and from the electrodes and from a computer 58 that is provided with a disc drive 60 and a monitor 62. Computer 58 is also provided with a keyboard (not shown) for use in controlling the operation of computer 58.

Figure 16:
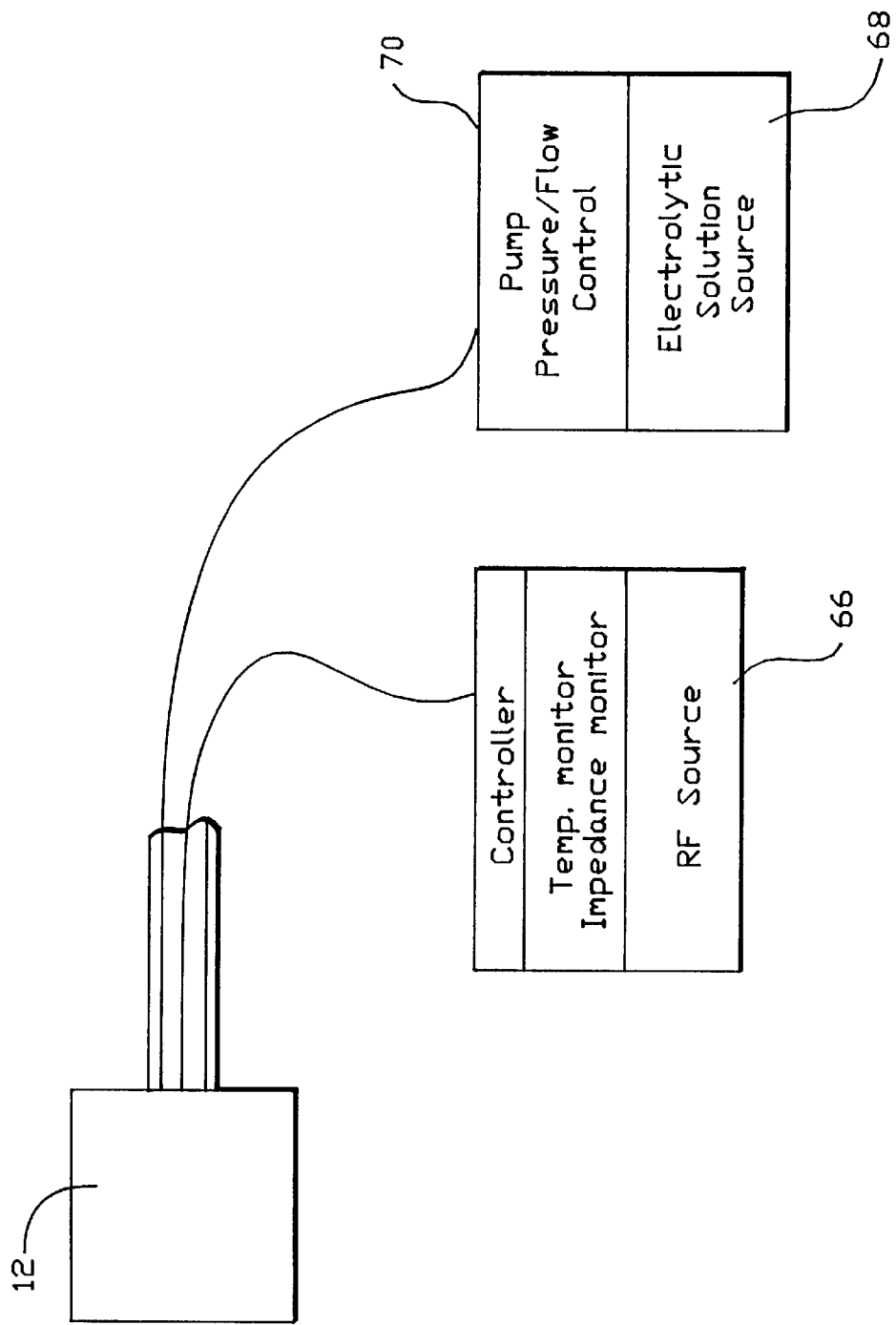
FIG. 16 is a block diagram of the cardiac ablation and mapping system of the invention.

As shown in FIG. 16, ablation system 10 can include an RF energy source 66 and an electrolytic solution source 68, all coupled to ablation apparatus 12. RF energy source 66 can incorporate a controller as well as both temperature and impedance monitoring devices. An output is associated with RF energy source 66.

Electrolytic solution source 68 can include a pump/ pressure flow control device 70, well known to those skilled in the art. A heating device for heating the electrolytic solution can be associated with electrolytic solution source 68. Suitable heating devices include, but are not limited to coils, bipolar RF electrodes, catalysts, and other devices.

Figure 17:
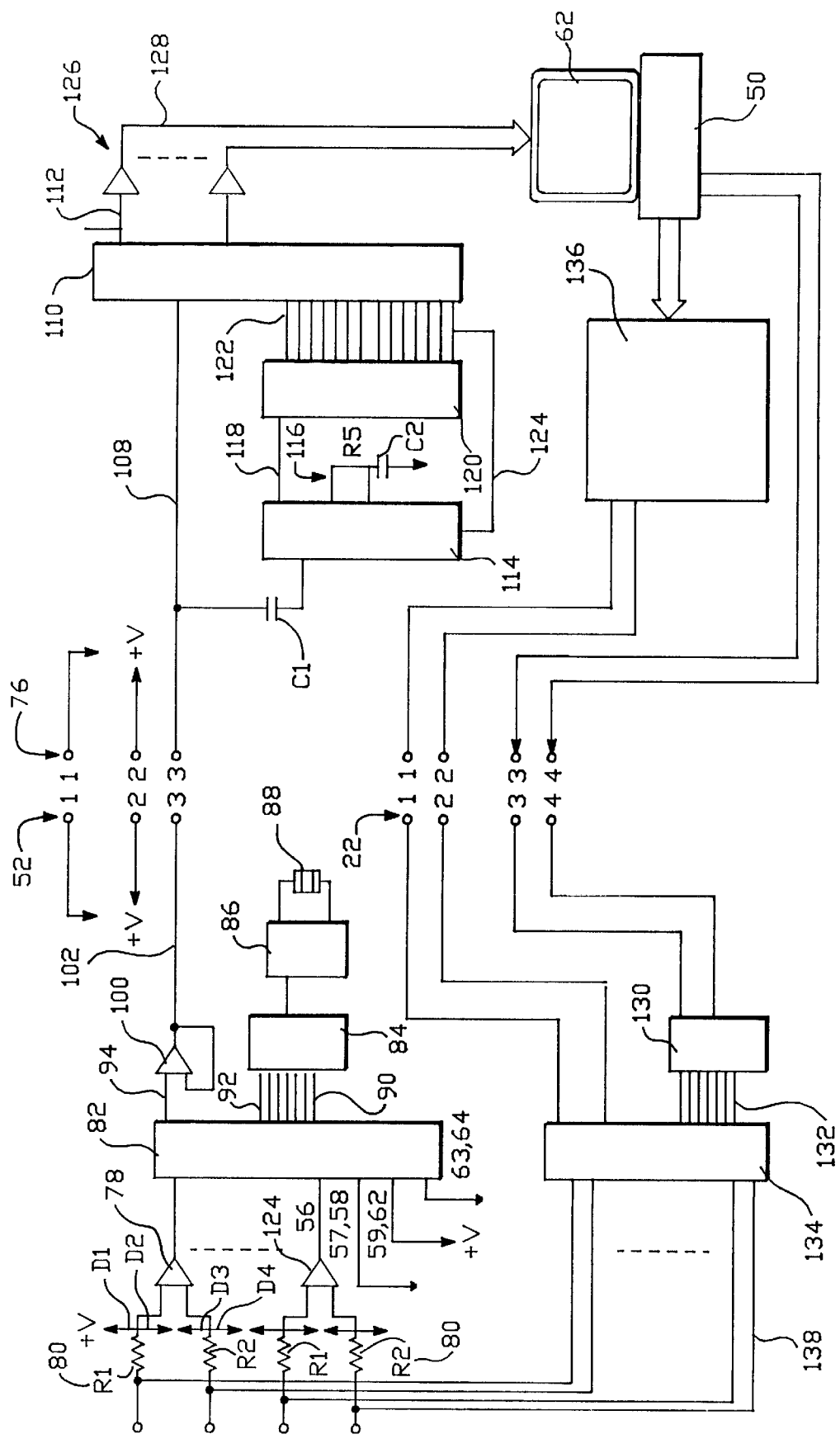
FIG. 17 is a circuit diagram of the cardiac ablation and mapping system of the invention.

Referring to FIGS. 15–17, as soon as distal end 30 of catheter 28 is positioned within the desired chamber, energy conduction connector 50 and signal connector 52 are interconnected with mating connectors 74 and 76, so that the plurality of electrodes are connected to interface module 54 and computer 58. Membrane 14 is then expanded by electrolytic solution causing membrane 14 to become distended and be self-retained in the heart.

Electrolytic solution in membrane 14 can be heated to a pre-selected temperature which can be modified and adjusted as necessary. For example, electrolytic solution can be heated and maintained at a temperature between about 40 to 50 degrees C. The electrolytic solution can be brought to a first temperature when it is introduced into membrane 14. The initial temperature of the electrolytic solution is insufficient to create tissue ablation. RF energy is delivered to selected RF electrodes 34 transferring thermal energy to surrounding electrolytic solution, which then contacts endocardial tissue causing a desired ablation effect. The amount of energy transferred from RF electrodes 34 to the surrounding electrolytic solution is sufficient to cause the surrounding electrolytic solution to become an electrode that transfers thermal energy to endocardial tissue and result in ablation. Providing pre-heated electrolytic solution to membrane 14 merely reduces the level of necessary RF energy delivered to RF electrodes.

Once this is accomplished, membrane 14 is in a contacting and conforming relationship to the wall of the chamber of the heart. Thermal energy is conducted through membrane 14 and to a selected tissue site of the heart chamber to cause ablation. When membrane 14 becomes expanded its exterior surface and recording electrodes 15 are in a contacting relationship with the wall of the chamber. Membrane 14 moves with the chamber with its constrained contraction and expansion. Lumen 26 in inner lumenal member 16 permits blood to flow in and out of the heart chamber.

Electrical resources acquire electrical data from the heart and provide electrical function feedback to RF generator 66. RF generator 66 then supplies a therapeutic output to RF electrodes 34. These electrical resources map the heart with recording electrodes 15 to acquire activation data, seek the origin of the arrhythmia, provide early local endocardium activation, provide ablation, further mapping, and further ablation if required.

Operation and use of cardiac ablation and mapping apparatus 12 in connection with interrace module 56 and computer 58 is now described.

In one specific embodiment, the plurality of RF electrodes 34 can be operated in the bipolar mode. Bipolar RF electrode pairs are connected to a differential amplifier 78. Each of the differential amplifiers 78 are provided with input circuitry 80, which consists of current limiting resistors R1 and R2 connected to diodes D1 and D2 on opposite sides of the input line, with the diode D2 being connected to ground and diode D1 being connected to a positive voltage. Diodes D4 and D6 are connected to the other input line with diode D4 being connected to ground and diode D6 being connected to the positive voltage. These serially connected diodes serve to protect the inputs to differential amplifiers 78 during the time that ablation voltages are being applied.

The input circuitry has the capability of limiting the voltage rise at the inputs of differential amplifiers 78 to approximately ½ volt. Differential amplifiers 78 have a suitable gain as for example typically between 100 and 500.

Outputs of differential amplifiers 78 are connected by a number of lines depending of the number of RF electrodes and pairs to an analog multiplexer 82. Multiplexer 82 can have a number of inputs, as for example, 64. Inputs are connected to circuit 38 at connector 44. Certain inputs can be grounded. While other inputs can be connected to a positive voltage supply. One or two of the inputs can be utilized for providing a synchronization signal for demultiplexing, as hereinafter described.

Multiplexer 82 is driven by a 6 bit binary counter 84, which is supplied with a clock frequency from an oscillator 86 that is controlled by crystal 88 of a suitable frequency as for example, 200 KHz. The 200 KHz oscillator frequency can provide a five microsecond cycle length per channel. Counter 84 supplies an output 90 on six lines 92 to multiplexer 82. Multiplexer 82 is provided with an output line 94 which is controlled by binary counter 84, so that the output from each of the amplifiers 78 appear on output line 94 for the five microsecond pulse length provided by oscillator 86.

Information can be received on as many as 56 channels with each channel having a 5 microsecond duration, followed by a synchronizing pulse that is 20 microseconds wide to complete one cycle of multiplexer 82 of 320 microseconds, followed by the next 320 microsecond cycle. This provides an effective sampling rate of about 3000 samples per second.

Output 94 is connected to a buffer amplifier 100 which provides its output 102 on pin 3 of connector 52. The other pins 1 and 2 in connector 52 are connected to ground and a plus voltage, respectively, in interface module 54.

A multiplexer chip 104 is connected to leads 106 which in turn are connected to selected RF electrodes 34 (FIG. 15). The power of multiplexer chip 104, associated with cardiac ablation and mapping apparatus 12, is supplied from interface module 54 through pins 1 and 2 of connector 76, as shown in FIG. 17. Pin 3 of connector 76 receives the output signal from pin 3 of connector 52 and supplies it through a line 108 to a demultiplexer 110. Demultiplexer 110 is supplied with a plurality of output channels 112. Assuming there are 64 input channels in multiplexer 82, there will be a corresponding number of output channels 112 in demultiplexer 110.

The information on line 108, containing the synchronizing signal, is also supplied through a capacitor Cl to a phase locked loop 114, and is connected to an RF filter network 116 consisting of a resistor R5 and a capacitor C2 connected to ground. Phase locked loop 114 is provided with an output line 118 and has provided thereon a reconstructed 200 KHz voltage controlled oscillator output which is supplied to a counter 120. Counter 120 is provided with a plurality of output lines 122 which are connected to demultiplexer 110. Lines 122 are provided with frequencies ranging from 100 KHz to 3,125 KHz, with the 3,125 being connected to phase locked loop 114 by a line 124 which serves to couple the VCO output to phase locked loop 114. The use of the phase locked loop 114 allows the reconstruction of the 200 KHz clock, which is synchronized to the 200 KHz in multiplexer chip 104.

Demultiplexer 110 serves to demultiplex the information supplied from multiplexer 82 and supplies it on the 56 channels 112 to circuitry 126; which includes sample and hold circuitry, filter circuitry and A/D converters, to provide an output on lines 128 in the form of a signal that is supplied to computer 58 and display monitor 62. Computer 58 is provided with software that has the capability of analyzing information being supplied to it by utilizing sampling techniques well known to those in the art. Computer 58 performs an analysis of the information including but not limited to mapping of the heart to acquire electrical activation data and early endocardial activation. With the use of propagation and delay time analysis computer 58 identifies and isolates the area within a heart chamber which may contain an arrhythmogenic focus to be ablated. This information is displayed on the screen of monitor 62 so that it can be reviewed by the physician who then decides whether or not ablation is desirable.

After the mapping has been accomplished by use of cardiac ablation and mapping apparatus 12 (recording electrodes 15), and an arrhythmogenic focus has been located, the same cardiac ablation and mapping apparatus 12, while still in place in the heart chamber, is used for accomplishing the ablation with electrolytic solution receiving RF energy from RF electrodes 34. The attending physician inputs the desired commands to the keyboard connected to computer 58 to give the command to proceed with an ablation. As soon as such a command is received by computer 58, it sends a channel number serially to pin 3 of connector 74; which is connected to the corresponding pin 3 of connector 50 in a serial to parallel shift register 130 that is disposed in electrode grid ablation apparatus 12. Shift register 130 supplies the channel number to demultiplexer 110 on the six lines 132 to a high voltage demultiplexer 134. Shift register 130 is provided with a clocking signal on pin 4 of connector 50 that is supplied with a clock signal on the corresponding pin 4 of connector 74 from computer 58.

The output of computer 58 is also connected to a high voltage ablation power supply 136. High voltage ablation power supply 136 is programmable as to channel number and the amount of energy to be supplied on the channel. High voltage ablation power supply 136 supplies its output to pins 1 and 2 of connector 74, connected to corresponding pins 1 and 2 of connector 50, which are connected to demultiplexer 134. Demultiplexer 134 is provided with high voltage transistors which can tolerate the ablation voltages supplied by ablation power supply 136. Ablation power supply 136 can supply a high voltage, high frequency (typically 50–100 volts at 750 KHz to 1 MHz) pulse across the pins 1 and 2 of connector 74. This high voltage pulse appears on the corresponding the pins 1 and 2 of connector 50, and is supplied by demultiplexer 134 to the appropriate channel and appropriate RF electrode 34 or RF electrode pair through lines 138 connected to leads 106. This pulse is transmitted across a RF electrode 34 or RF electrode pair, and causes an ablation, of suitable depth, to occur in the endocardium of the right atrium. Alternatively, ablation can be accomplished between one or more RF electrodes 34 and an external ground RF electrode placed on the chest of the patient. In this manner, it can be seen that a highly controlled ablation is provided which is precisely positioned with respect to the selected RF electrodes 34 which can be multiplexed, and a maze type of ablation can be produced.

Several milliseconds after the ablation pulse has been supplied to the appropriate RF electrode or electrode pair, mapping can again be resumed to ascertain whether or not arrhythmogenic foci are still present. If the mapping indicates that atrial fibrillation is inducible additional pulses can be programmed by computer 58 and supplied to other appropriate RF electrodes 34 until the arrhythmias can no longer be initiated.

Programmed stimulation can be performed by using a selectable number of recording electrodes 15. In this mode of operation, interface 54 provides a programmable level of low voltage pulses (5–10 volts) via the high voltage connector 58 to stimulate the heart with synchronized pulses in order to induce or convert an arrhythmia.

Staggered radiopaque markers can be utilized to ascertain which segments 40 are located closest to the anatomical point of interest in the heart cavity, as for example, the right atrium. By observing this staggered relationship of the markers, the physician can select the signals coming from a specific segment 40 to analyze the same in computer 58.

Cardiac ablation and mapping apparatus 12 can be provided with an increased number or decreased number of RF electrodes 34 if desired. Any number of channels can be readily provided in multiplexer 82 and demultiplexer 110. The shape of circuit segments 40 can be made so that they conform to the wall of the heart, through membrane 14, as it expands and contracts through the entire cardiac cycle. Segments 40 do not directly touch the wall of the heart chamber. Instead, they are preferably formed on the exterior of inner lumenal member 16. Membrane 14 maintains intimate contact with the wall of the heart chamber, minimizing the amount of energy which is dissipated into the blood pool within the cavity of the heart during ablation.

Once the desired procedures are completed, cardiac ablation and mapping apparatus 12 is removed from the heart chamber.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A cardiac ablation device for ablating tissue within a chamber of the heart, comprising:
    an introducer catheter;
    a plurality of RF electrodes;
    a fluid permeable expandable member surrounding the electrodes;
    a member support attached to the expandable member, the member support, catheter and fluid permeable expandable member being arranged so as to allow blood flow through the heart chamber when the expandable member is expanded adjacent to the chamber;
    an electrical connector device connecting the electrode to an RF energy source; and
    a source adapted to provide an electrolytic fluid to the expandable member to expand the expandable member to conform to at least a portion of the heart chamber and to cause said fluid to create a thermal path between the electrodes and an inner surface of the heart chamber.

2. The ablation apparatus of claim 1, further comprising:
    electrical resources for acquiring electrical data from the heart and providing electrical function feedback to the RF power source which then supplies a therapeutic output to selected treatment electrodes of the plurality.

3. The ablation apparatus of claim 2, wherein the electrical resources includes devices for supplying a predetermined voltage at a predetermined frequency to heat the electrolytic solution to cause ablation in a preselected location in the wall of the heart chamber.

4. The ablation apparatus of claim 1, wherein the circuit is multiplexed.

5. The ablation apparatus of claim 1, wherein the membrane is secured to a distal end of the catheter for insertion into and removal from the heart chamber.

6. The ablation apparatus of claim 1, wherein the membrane includes a deposition of ions to improve RF and thermal energy conductivity.

7. The ablation apparatus of claim 1, wherein the plurality of treatment electrodes are positioned in a spaced apart relationship from the conductive surface.

8. An endocardial ablation apparatus for introduction into a heart chamber formed by a wall, comprising:
   an expandable, flexible, fluid permeable member adapted to receive an electrolytic solution and become expanded to substantially conform a surface of the member to a surface within a heart chamber;
   a catheter for introducing the member into a heart chamber in a non-expanded state;
   a membrane support attached to the member, the membrane support, catheter and fluid permeable member being constructed so as to allow blood flow through the heart chamber when the fluid permeable member is expanded adjacent to a chamber wall;
   means for delivering an electrolytic solution to the member to expand the member;
   a plurality of treatment electrodes covered by the member;
   an RF power source coupled to the treatment electrodes; and
   a source of electrolytic solution fluidly coupled to the member, the solution coupling RF and thermal energy sufficient to ablate a portion of the tissue to the heart chamber.

9. The ablation apparatus of claim 8, further comprising:
   electrical resources for acquiring electrical data from the heart and providing electrical function feedback to the RF power source which then supplies a therapeutic output to selected treatment electrodes of the plurality.

10. The ablation apparatus of claim 9, wherein the electrical resources includes devices for supplying a predetermined voltage at a predetermined frequency to heat the electrolytic solution to cause ablation in a preselected location in the wall of the heart chamber.

11. The ablation apparatus of claim 8, wherein the circuit is multiplexed.

12. The ablation apparatus of claim 8, wherein the member is secured to a distal end of the catheter for insertion into and removal from the heart chamber.

13. The ablation apparatus of claim 8, wherein the member includes a deposition of ions to improve RF and thermal energy conductivity.

14. An endocardial ablation apparatus for introduction into a heart chamber formed by a wall, comprising:
   an inflatable, flexible porous membrane adapted to receive an electrolytic solution and become inflated to substantially conform an exterior surface of the membrane to the wall of the heart chamber;
   a membrane support attached to the membrane;
   an introducer catheter that introduces the membrane and membrane support into a selected heart chamber, said catheter, membrane support and porous membrane being constructed to permit blood flow through the heart chamber when said porous membrane is inflated adjacent to the wall in the heart chamber;
   a plurality of RF electrodes defining a circuit positioned in or surrounded by the membrane, the RF electrodes transferring thermal energy to the electrolytic solution providing an ablation of a selected site of the heart chamber;
   an RF power source coupled to the RF electrodes; and
   a source of electrolytic solution coupled to the membrane for coupling thermal energy to the selected site.

15. The ablation apparatus of claim 14, wherein the membrane support comprises an inner lumenal member including a lumen that permits blood flow through the inner lumenal member and the heart chamber, and wherein the plurality of RF electrodes are positioned on the exterior surface of the inner lumenal member.

16. The ablation apparatus of claim 15, wherein the lumen extends along a longitudinal axis of the inner lumenal member.

17. The ablation apparatus of claim 15, wherein the lumen does not pass blood through the inner lumenal member to the membrane.

18. The ablation apparatus of claim 15, wherein the membrane and the inner lumenal member include a plurality of adjacently positioned apertures permitting blood flow at an inlet of the superior vena cava, an inlet of the inferior vena cava, and at the tricuspid valve annulus.

19. The ablation apparatus of claim 15, wherein the plurality of RF electrodes are positioned between the exterior surface of the inner lumenal member and the exterior surface of the membrane.

20. The ablation apparatus of claim 14, further comprising:
   electrical resources in electrical communication with the RF electrodes for acquiring electrical data from the heart and providing electrical function feedback to the RF power source which then supplies a therapeutic output to selected RF electrodes of the plurality.

21. The ablation apparatus of claim 20, wherein the RF power source supplies a bipolar therapeutic output to selected RF electrodes such that the apparatus operates in a bipolar mode.

22. The ablation apparatus of claim 20, wherein the electrical resources includes members for recording mapping potentials encountered by the RF electrodes.

23. The ablation apparatus of claim 20, wherein the electrical resources includes devices for supplying a predetermined voltage at a predetermined frequency to selected RF electrodes to cause ablation in a preselected location in the wall of the heart chamber.

24. The ablation apparatus of claim 14, further comprising:
   a plurality of recording electrodes positioned on an exterior surface of the support member.

25. The ablation apparatus of claim 24, wherein the membrane support comprises an inner luminal member including a lumen and wherein the RF electrodes are positioned on an exterior surface of the inner luminal member.

26. The ablation apparatus of claim 14, further comprising:
   a ground pad electrode attached to an exterior surface of a patient.

27. The ablation apparatus of claim 14, wherein the circuit is a flexible circuit.

28. The ablation apparatus of claim 14, wherein the plurality of RF electrodes are multiplexed.

29. The ablation apparatus of claim 14, wherein the circuit is multiplexed.

30. The ablation apparatus of claim 14, wherein the membrane is rolled around the introducer catheter distal end for removal from the heart chamber.

31. The ablation apparatus of claim 14, wherein the circuit includes one or more impedance monitors.

32. The ablation apparatus of claim 14, wherein the circuit includes one or more temperature monitors.

33. The ablation apparatus of claim 14, wherein the circuit includes one or more devices to monitor circuit continuity.

34. The ablation apparatus of claim 14, wherein the circuit includes a plurality of segments.

35. The ablation apparatus of claim 14, wherein the membrane includes a deposition of ions to improve RF and thermal energy transfer.

36. The ablation apparatus of claim 14, wherein the exterior surface of the membrane is coated with an anticoagulating material.

* * * * *